United States Patent [19]

Herbert

[11] 4,302,437
[45] Nov. 24, 1981

[54] MITOGEN STIMULATED LYMPHOCYTE TRANSFORMATION

[76] Inventor: Victor Herbert, 88 Walworth Ave., Scarsdale, N.Y. 10583

[21] Appl. No.: 71,357

[22] Filed: Aug. 30, 1979

[51] Int. Cl.$^3$ .................... G01N 33/60; G01T 1/00
[52] U.S. Cl. .................... 424/1; 23/230 B; 424/2; 435/6
[58] Field of Search ............ 424/1, 12, 2; 23/230 B; 422/61; 435/6

[56] References Cited

PUBLICATIONS

Das et al., Clin. Chem., vol. 26, No. 1, 1980, pp. 72–77.
Das et al., Clin. Res., vol. 26, 1978, p. 618A.
Park et al., Proc. Natl. Acad. Sci. USA, 99, 371–373, (1972).
Pellegrino, Clin. Immunol. Immuno Pathol., 2, 67–73, (1973).
Junge et al., Clin. Exp. Immunol., 7, 431–437, (1970).

Primary Examiner—Christine M. Nucker
Attorney, Agent, or Firm—Louis E. Marn; Elliot M. Olstein

[57] ABSTRACT

Mitogen stimulated transformation of blood lymphocytes is effected with a whole blood sample of a quantity of no greater than 0.5 ml, and a mitogen to whole blood sample ratio which prevents agglutination of blood cells to thereby facilitate uniform uptake of reagents by the lymphocytes in subsequent testing. Lymphocyte transformation can be measured by use of a radioisotope, and the technique is particularly suitable for measuring vitamin deficiency by a dU or thymidine suppression test, or for determining lymphocytic malignancy. The use of a whole blood culture eliminates lymphocyte separation, and the use of micro quantities of blood extends clinical application to routine laboratories and pediatric patients.

30 Claims, No Drawings

MITOGEN STIMULATED LYMPHOCYTE TRANSFORMATION

Mitogen stimulated transformation of blood lymphocytes in culture has been extensively used for cytogenetic, immunological and metabolic studies. Such transformation of blood lymphocytes is commonly measured by the use of a radioisotope, and in particular a radioactive nucleoside; e.g., $^3$H-, or $^{14}$C-thymidine incorporation into newly synthesized DNA. The mitogen stimulated culture of lymphocytes has also been used as a model system for measuring cellular folate or vitamin $B_{12}$ status, and for the dU or thymidine suppression test. The dU suppression test measures the efficiency of the de novo pathway of thymine-DNA synthesis, and is a sensitive biochemical index of megaloblastosis, and underlying vitamin deficiency. The thymidine suppression test measures the salvage pathway of DNA synthesis. In the conventional procedure for mitogen stimulated transformation of blood lymphocytes, lymphocytes are separated from whole blood using various micromolecular gradients or filtration through a cotton or nylon column, a process which is time consuming, entails loss of lymphocytes and requires a large quantity of blood.

Park, et al, "A New Micromethod for Evaluating Lymphocyte Responses to Phytohemagglutinin: Quantitative Analysis of the Function of Thymus-Dependent Cells," Proc. Nat. Acad. Sci. USA 69:371, 1972, discloses mitogen stimulated transfer in a whole blood sample to eliminate lymphocyte separation, and after study with PHA-M mitogen to whole blood ratios which vary from 100 to 10,000 μg of PHA-M per 1 ml of whole blood (10–1000 μg per 0.1 ml of whole blood), the article concludes that a PHA-M mitogen to whole blood ratio of 1000 μg per ml of whole blood (100 μg per 0.1 ml of blood) is optimum.

Applicant has found that mitogen stimulated lymphocyte transformation can be conducted in a whole blood sample of microquantity with an amount of mitogen to induce lymphocyte transformation and provide a mitogen to whole blood ratio which prevents blood cell agglutination. In general, the sample quantity is no greater than 0.5 ml and the mitogen to whole blood ratio does not exceed 40 μg mitogen per 0.1 ml of whole blood. Based on this finding, applicant has developed new tests which involve lymphocyte transformation which can be conducted in whole blood samples rather than with separated lymphocytes.

More particularly, applicant has developed a new and improved test for lymphocytic malignancy and a new and improved deoxyuridine and thymidine suppression tests and kits which employ whole blood in a quantity of no greater than 0.5 ml in which lymphocyte transformation is induced by a mitogen in a quantity sufficient to induce mitosis and provide a mitogen to whole blood ratio which prevents blood cell agglutination.

Blood lymphocyte transformation (mitogenesis) may be stimulated by any one of a wide variety of mitogens. As representative examples of such mitogens, there may be mentioned lectins, such as phytohaemagglutinin (PHA), (PHA-P, PHA-M; PHA-W, etc.), pokeweed mitogen, etc.; antigens to which lymphocytes have been previously exposed, such as candida, mumps, measles, etc.; anti sera, such as, Rabbit anti- MOLT-4, anti-B411-4 cells sera; etc.; and miscellaneous materials, such as sodium periodate, zinc chloride, calcium ionophore A23187, Concanavalin A, and the like. The selection of a suitable mitogen is deemed to be well within the scope of those skilled in the art from the teachings herein.

Lymphocyte transformation can be measured by the use of an appropriately labelled material which is a precursor or component of the product produced by the transformation of the lymphocyte. Such lymphocyte transformation is then measured by determining the amount of labelled material in the resulting product. The labelling may be conveniently accomplished by the use of a radioactive isotope; however, it is also possible to accomplish such labelling by the use of, for example, a fluorescent material, an enzyme, or the like. In most cases, the material is a radioisotope labelled precursor or component of DNA, with such DNA being produced in the lymphocyte transformation. Radioisotope labelled thymidine or radioisotope labelled deoxyuridine may be conveniently employed for measuring such lymphocyte transformation; however, the use of other labelled materials, and in particular radioisotope labelled materials is possible within the spirit and scope of the present invention. The selection of a suitable label is deemed to be well within the scope of those skilled in the art from the teachings herein.

The mitogen stimulated transformations of blood lymphocytes in culture is conducted by the technique generally known in the art, as modified in accordance with the present invention by the use of a microquantity of a whole blood sample and by the use of specified quantities of mitogen. As hereinabove noted, the whole blood sample is employed in a quantity of no greater than 0.5 ml, with the whole blood sample generally being of a quantity of at least 0.01 ml. The preferred sample size is 0.1 ml. As hereinabove noted, the mitogen is employed in an amount to induce the lymphocyte transformation, and provide a mitogen to whole blood sample ratio which prevents blood cell agglutination, generally a ratio which does not exceed 40 μg mitogen per 0.1 ml of whole blood sample, although, in some cases, particularly where weaker mitogens are employed, greater ratios can be employed. In general, the mitogen is employed in an amount of at least 5 μg per 0.1 ml of whole blood sample. The mitogen is preferably employed in a quantity of 20 μg per 0.1 ml of whole blood sample. The mitogen stimulated transformation of whole blood in culture is generally conducted at a temperature in the order of from 23° C. to 40° C., preferably at 37° C., for a time period sufficient to induce the lymphocyte transformation, generally a time period in the order of from 2 to about 9 days. The lymphocyte transformation may be evaluated by measuring incorporation of a suitably labelled material into the transformation product. Thus, for example, as hereinabove noted, such evaluation may be conveniently accomplished by measuring incorporation of a radioisotope labelled material into DNA. In particular, after incubation with the mitogen (2–9 days as appropriate), radioisotope is added, and incubation continued for a short pulse period; e.g., 1–4 hours. The reaction is then terminated and radioactivity determined.

After incubation, as known in the art, the reaction is stopped; e.g., by the addition of cold isotonic saline, and the cells centrifuged. The cells are then lysed; e.g., by distilled water, and DNA precipitated; e.g., by trichloroacetic acid (TCA) after hemoglobin removal.

As hereinabove noted, the mitogen stimulated transformation of blood lymphocytes in whole blood may be employed for conducting a dU suppression test. As known in the art, dU suppression test is based on the ability of dU to suppress subsequent incorporation of a radioactive nucleoside into DNA in mitogen stimulated lymphocyte transformation, with such dU suppression occurring in the absence of a vitamin deficiency; e.g., dU does not suppress such incorporation as well when there is a vitamin deficiency ($B_{12}$ and/or folate). In the dU suppression test, each of appropriate samples are incubated with a mitogen to stimulate transformation of blood lymphocytes. After a suitable incubation period to induce lymphocyte transformation as hereinabove described, the first sample is incubated in the presence of dU and absence of any added vitamin, the second sample in the presence of dU and added hydroxocobalamin, the third sample in the presence of dU and added methyltetrahydrofolate, and the fourth sample in the presence of dU and both added hydroxocobalamin and methyltetrahydrofolate, followed by incubation with a radiolabelled nucleoside. The results obtained with each of the four samples is then compared with a control sample (mitogen stimulated whole blood culture in the presence of radiolabelled nucleoside having no vitamin deficiency, and without preincubation with dU), and if there is no vitamin deficiency in the blood sample, then the first sample will have less than 20% of the radioactivity of the control sample; i.e., the dU suppresses the incorporation of the radioactive nucleoside into DNA when there is no vitamin deficiency. If the first sample has a radioactivity in excess of 20% of the radioactivity of the control sample, then the dU did not adequately suppress the incorporation of the radiolabelled nucleoside into the DNA, and there is a vitamin deficiency. Samples 2, 3 and 4 are then compared with the control sample in order to ascertain whether the deficiency is in vitamin $B_{12}$, folate or both. Sample 2 has added $B_{12}$, and if sample 2 has a radioactivity less than 20% of the radioactivity of the control sample, then the vitamin deficiency is in $B_{12}$. Sample 3 contains added folate, and if sample 3 has a radioactivity which is less than 20% of the control sample, then the vitamin deficiency is in folate. If neither sample 2 nor sample 3 has a radioactivity which is less than 20% of the radioactivity of the control sample, and sample 4 has a radioactivity of less than 20% of radioactivity of the control sample, then the sample has a vitamin deficiency in both folate and vitamin $B_{12}$. In accordance with the present invention, the dU suppression is effected with whole blood, rather than separated lymphocytes, and such whole blood sample is employed in microquantities, i.e., a quantity of no greater than 0.5 ml, and preferably 0.1 ml, with a controlled quantity of mitogen; i.e., a quantity of mitogen sufficient to induce lymphocyte transformation and provide a mitogen to whole blood sample ratio of generally no greater than 40 µg per 0.1 ml of whole blood sample. In addition, the test is conducted with reduced quantities of dU, with the dU being employed in an amount of less than 5 µmol, generally less than 3 µmol, with the dU generally being present in an amount of at least 1 µmol and preferably in an amount of 2 µmol, all based on 1 ml of total culture (blood plus culture medium). The use of greater amounts of dU may prevent successful operation of the test.

In conducting the dU suppression test in accordance with the present invention, applicant has found that the best results can be obtained by the use of a whole blood sample of 0.1 ml, phytohemagglutinin as a mitogen, preferably in an amount of 20 µg per sample, with the peak-time response of radionucleoside incorporation occurring on day 4; i.e., the test is conducted after mitogen stimulation for four days. In general, the amount of dU for causing suppression of nucleoside incorporation into the DNA; in particular, $^3$H-thymidine or $^{125}$I-dU, to less than 10% of the control in whole blood was at least 5 µmol.

The procedure of the present invention is also applicable to a thymidine suppression test, which is conducted as described with respect to the dU suppression test, except that preincubation is conducted with thymidine instead of dU and the tracer is radioisotope labelled deoxyuridine.

Lymphocytic malignancy may be determined by measuring incorporation of a suitably labelled material into DNA; in particular, a radioisotope labelled material; i.e., radiolabelled nucleoside; in particular, radiolabelled thymidine or radiolabelled deoxyuridine. In accordance with the procedure of the invention, the lymphocytic malignancy test is conducted with whole blood and with a mitogen in the amounts as hereinabove described. In using whole blood as hereinabove described, peak incorporation in malignant lymphocytes occurs on day 8 as contrasted to day 4 with normal lymphocytes. Thus, lymphocytic malignancy in a sample can be determined by comparing the isotope incorporation on a given day with the isotope incorporation in a normal standard. The lymphocytic malignancy test is conducted by the procedure for measuring lymphocyte transformation, as hereinabove described, with there being a delayed lymphocyte transformation, as determined by radioisotope incorporation into DNA when lymphocytes are malignant.

The invention will be further described with respect to the following example; however, the scope of the invention is not to be limited thereby:

EXAMPLE 1

Blood was collected from clinically and hematologically healthy volunteers in sterile silicone-coated heparinized vacutainer tubes. An aliquot was removed for total and differential leucocyte counts, from which the total lymphocyte count was determined. The remaining heparinized blood was diluted in 1 in 10 with Trisbuffered Hanks-Eagle solution (pH 7.4, 0.06 M) containing 200 unit each of penicillin and streptomycin/ml. One ml aliquots containing 0.1 whole blood and 0.9 ml of Tris Hanks-Eagle medium (Microbiological Associates, Bethesda, Md.) was dispensed in 10 ml sterile silicone-coated vacutainers (Becton-Dickinson & Co., Rutherford, N.J.). The content of a vial of Bactophytohaemagglutinin-P (PHA-P (PHA-P Difco; Detroit, Mich.) (100 mg) was dissolved in 5 ml of Tris-Hanks balanced salt solution (THBSS) (purchased from Microbiological Associates, Bethesda, Md.). This 5 ml containing 20 mg PHA-P/ml, was further diluted with THBSS. Aliquots of different dilutions were kept frozen at $-20°$ C. At the time of use, these were thawed, and 0.1 ml of each dilution was added to the culture. The PHA solutions, once thawed, were discarded. Cultures were set up in triplicate and incubated at 37° C. for different periods up to 5–6 days. Lymphocyte transformation was evaluated by measuring incorporation of $^3$H-thymidine ($^3$H-TdR) or $^{125}$I-deoxyuridine ($^{125}$I-UdR) into DNA. ($^{125}$I-deoxyuridine may deteriorate unexpectedly. Prior to each use, a sample of 50 µl of $^{125}$I-UdR is added to 0.5 ml of a 0.025 gm% solution of haemoglobin-coated charcoal and 1 ml of Tris-Hanks, briefly shaken and then centrifuged. If less than 90% of the radioactivity is taken up by the coated charcoal, the material should be considered deteriorated and should be discarded). A short pulse of 3 hours with 1μCi (50 μl) of $^3$H-TdR (specific activity=23 Ci/mmol, Amersham Searle, Arlington Heights, Ill.) and 1μCi (50 μl of $^{125}$I-UdR (specific activity=2 mCi/mg, Amersham Searle, Arlington Heights, Ill.) was given to two separate sets of triplicate cultures from each sample of blood.

After incubation the reaction was stoped by adding 5 ml of cold isotonic saline. Then cells were centriguged at 4° C. at 2000 rpm for 10 min and the supernatant discarded. The red cells were shock lysed by the addition of 4.5 ml cold distilled water followed by the addition of 1.5 ml of 3.5% NaCl solution. This was centrifuged at 2000 rpm at 4° C. for 15 min and the supernatant discarded. 5 ml of 3% acetic acid solution was then added to the pellet, vortexed and centrifuged at 2000 rpm for 15 min. The pellet was then washed once with cold normal saline. After removing the supernatant, 5 ml of 10% cold TCA was added to the pellet, centrifuged, and the supernatant discarded. 0.5 ml of Soluene TM 100 (purchased from Packard Instruments, Downers Grove, Ill.), was then added to each tube containing the TCA precipitated pellet. The dissolved pellet was then washed into a scintillation vial with 10 ml of Instra-gel scintillation liquid (Packard, Downers Grove, Ill.). The radioactivity was measured in a Packard Liquid Scintillation Counter, and disintegration per minute (dpm) obtained by quench correction using an external standard.

Cultures in which $^{125}$I-UdR was used as the tracer nucleoside, were processed in a slightly different, but simpler manner. After the step of shock lysis of red cells with distilled water followed by the addition of 3.5% saline solution, the pellet was washed once again with cold isotonic saline. To the washed pellet was added 5 drops of salt-free albumin solution and 5 ml of 10% TCA. This was centrifuged at 2000 rpm at 4° C. for 10 min, the supernatant decanted and the radioactivity of the pellet read in a Packard Autowell Gamma counter.

The use of the above procedure with different concentrations of PHA-P indicated that when the mitogen concentration exceeded 40 μg per 0.1 ml whole blood, there was significant clumping of red blood cells, which results in a grossly erratic uptake of reagents by lymphocytes in subsequent incubation. The experiments also indicated that peak incorporation of the radionucleosides occurred on day 4.

EXAMPLE 2 dU SUPPRESSION TEST

Whole blood cultures, as in Example 1, were preincubated with varying concentrations of dU with and without PteGlu, 5-methyl H$_4$-folate, or vitamin B$_{12}$ for 1 hr, followed by 3 hr incubation with 1μCi of $^3$H-TdR or $^{125}$I-UdR on day 4, (corresponding to the day of peak PHA response). The reaction was then stopped by the addition of 5 ml cold isotonic saline, and the subsequent procedure of washing and extraction of DNA was as in Example 1. The results of dU suppression are expressed as the percentage incorporation of $^3$H-TdR or $^{125}$I-UdR into DNA in the presence of added dU as compared to the incorporation of these nucleosides in replicate cultures (controls) to which no dU was added.

It was found that the dU suppression test can be performed by curtailing the period of incubation of the cultures to 1 hr subsequent to the addition of the radioactive nucleosides ($^{125}$I-UdR or $^3$H-TdR). The results of dU suppression of $^3$H-TdR or $^{125}$I-UdR incorporation into DNA followed this short period of incubation were similar to those obtained in the earlier procedure in which the incubation period was 3 hrs.

As expected, preincubation with different concentration of deoxyuridine decreased the incorporation of subsequently added $^3$H-TdR or $^{125}$I-UdR into DNA in the whole blood culture. The addition of 1 to 10 μmol of deoxyuridine per culture tube suppressed $^3$H-TdR or $^{125}$I-UdR incorporation into DNA to about 10% of control culture (i.e., replicate cultures to which no dexyuridine was added). The results of these experiments with whole blood culture were similar to those with purified lymphocyte cultures from the same donors. In ten normal subjects, the addition of folic acid (PteGlu), 5-methyl H$_4$ folate, cyano-, and hydroxocobalamin had no effect on the deoxyuridine (dU) suppression of $^3$H-TdR or $^{125}$I-UdR incorporation into DNA either in the whole blood culture or purified lymphocyte culture, thus affirming the normal status of these subjects with respect to vitamin B$_{12}$ and folic acid.

The following is a tabular presentation of the procedure for a dU suppression test:
1. Do cell count.
2. Prepare slide of blood smear for file.
3. Set up culture as follows:
    Each tube contains:
        0.1 ml of whole blood
        0.9 ml of Eagle's medium, and
        0.1 ml of PHA (20 μg PHA)
    Note: Whole blood and Eagle's medium can be mixed prior to addition to each tube.
4. Rack-mix culture, incubate 37° C. for 4 days
5. On the 4th day, incubate replicate cultures for 1 h.
    i. without dU
    ii. with dU alone
    iii. with dU+methyl-H$_4$-folate
    iv. with dU+B$_{12}$ (in hydroxocobalamin form)
    v. with dU+B$_{12}$+methyl-H$_4$-folate.
6. Add 50 μl=1μCi tritium labelled thymidine ($^3$H)-TdR) or $^{125}$I-labelled deoxyuridine ($^{125}$I-UdR) to each tube, rack-mix, and incubate for 3H. in a 37° C. water bath.

($^3$H)-TdR Washing procedure

1. Add 6.0 ml of cold saline to each tube, mix, spin at 2000 rpm, 10 min. Aspirate and discard supernate.
2. Add 4.5 ml of distilled water, mix, add 1.5 ml of NaCl, (35 g/L) mix, spin at 2000 rpm, 10 min. Aspirate and discard supernate.
3. Add 4.0 ml of acetic acid (30 mL/L), mix, spin at 2000 rpm, 10 min. Aspirate and discard supernate.
4. Add 6.0 ml of cold saline, mix, spin at 2000 rpm, 10 min. Aspirate and discard supernate.
5. Add 4 ml of TCA 100 g/L., mix, spin, aspirate and discard supernate.
6. Add 0.5 ml of sample solubilizer (Soluene), vortex, mix add 5.0 ml of liquid scintillation cocktail (Instagel) to each tube, mix, let stand overnight. Then add an additional 5 ml of Instagel and count. (Count a standard with each tube.)

($^{125}$I) UdR Washing Procedure

1. Add 6.0 ml of cold saline, to each tube, mix, spin at 2000 rpm, 10 min. Aspirate and discard supernate.

2. Add 4.5 ml distilled water, mix, add 1.5 ml of NaCl (35 g/L) mix, spin at 2000 rpm. Aspirate and discard supernate.
3. Add 6.0 ml of saline, mix, spin at 2000 rpm. Aspirate and discard supernate.
4. Add four drops of albumin with a syringe and 4.0 ml of TCA (100 g/L) mix, spin at 2000 rpm for 10 min. Decant supernate and count the pellet.

Count a standard with each experiment.

The above procedure is also applicable to a thymidine suppression with the incubation on the fourth day being conducted with thymidine in place of dU, as indicated, and the radioisotope being ($^{125}$I) UdR.

The present invention is an improvement over the prior art techniques in that it eliminates the necessity to employ large quantities of blood as required in cultures of purified lymphocytes. In accordance with the present invention, no more than 0.5 ml, and preferably 0.1 ml of whole blood per culture tube is required. The method is simple, requires minimal quantity of blood, avoids time consuming lymphocyte separation and purification, and involves minimal manipulation. This makes it possible to use heel- or finger-prick blood from pediatric patients. Applicant has found that the results with the present invention are comparable in consistency, reproducibility and magnitude to those obtained in cultures of purified lymphocytes from the same donors. In particular, the results of dU suppression of radionucleoside incorporation into DNA in the whole blood culture in accordance with the present invention were similar to those obtained in cultures of purified lymphocytes from the same donors. By employing the present invention, a routine laboratory can conduct a dU suppression test, study in vitro immune response, and demonstrate the delayed peak time response of malignant lymphocytes. In conducting the tests, clumping of blood cells is minimized which facilitates uniform uptake of reagents by the lymphocytes in subsequent testing.

Numerous modifications and variations of the present invention are possible in light of the above teachings and, therefore, within the scope of the appended claims, the invention may be practised otherwise than as particularly described.

I claim:

1. In a process for determining vitamin deficiency by a deoxyuridine suppression test wherein a blood sample is preincubated with a mitogen to stimulate transformation of blood lymphocytes to produce DNA, followed by incubation with deoxyuridine and tracer, the improvement comprising:
    employing a whole blood sample of a quantity of no greater than 0.5 ml, and mitogen in an amount to stimulate transformation of lymphocytes in the whole blood sample and provide a mitogen to whole blood sample ratio which prevents agglutination of blood cells.

2. The process of claim 1 wherein the incubation with deoxyuridine is conducted after mitogen stimulation for a period sufficient to induce peak mitogen response.

3. The process of claim 1 wherein the incubation with deoxyuridine is conducted after mitogen stimulation for a period of four days.

4. The process of claim 1 wherein the tracer is ($^{125}$I) deoxyuridine.

5. The process of claim 4 wherein the tracer and sample are incubated for from 1 to 4 hours.

6. The process of claim 1 wherein the tracer is ($^3$H) thymidine.

7. The process of claim 6 wherein the tracer and sample are incubated for from 1 to 4 hours.

8. The process of claim 1 wherein the whole blood sample quantity is 0.1 ml.

9. The process of claim 8 wherein the mitogen is employed in an amount of 20 μg per 0.1 ml of whole blood sample.

10. The process of claim 9 wherein the mitogen is PHA.

11. The process of claim 10 wherein the tracer is ($^{125}$I) deoxyuridine.

12. The process of claim 10 wherein the tracer is ($^3$H) thymidine.

13. In a process for determining vitamin deficiency by a thymidine suppression test wherein a blood sample is preincubated with a mitogen to stimulate transformation of blood lymphocyte to produce DNA, followed by incubation with thymidine and tracer, the improvement comprising:
    employing a whole blood sample of a quantity of no greater than 0.5 ml and mitogen in an amount to stimulate transformation in the whole blood sample and provide a mitogen to whole blood sample ratio which prevents agglutination of blood cells.

14. The process of claim 13 wherein incubation with thymidine is conducted after mitogen stimulation for a period sufficient to induce peak mitogen response.

15. The process of claim 13 wherein incubation with thymidine is conducted after mitogen stimulation for a period of four days.

16. The process of claim 13 wherein the tracer is ($^{125}$I) deoxyuridine.

17. The process of claim 13 wherein the whole blood sample quantity is 0.1 ml.

18. The process of claim 17 wherein the mitogen is employed in an amount of 20 μg per 0.1 ml of whole blood.

19. The process of claim 18 wherein the mitogen is PHA.

20. In a process for determining lymphocytic malignancy by determining delayed mitogen stimulated lymphocyte transformation, wherein a blood sample is preincubated with a mitogen to stimulate transformation of blood lymphocytes to produce DNA followed by incubation with a tracer, the improvement comprising:
    employing a whole blood sample of a quantity of no greater than 0.5 ml and mitogen in an amount to stimulate transformation in the whole blood sample and provide a mitogen to whole blood sample ratio which prevents agglutination of blood cells.

21. The process of claim 20 wherein the whole blood sample quantity is 0.1 ml.

22. The process of claim 21 wherein the mitogen is employed in an amount of 20 μg per 0.1 ml of whole blood.

23. The process of claim 22 wherein the mitogen is PHA.

24. The process of claim 1 wherein the deoxyuridine suppression test is effected by incubation with deoxyuridine in an amount of less than 5 μmol, based on 1 ml of total blood culture.

25. The process of claim 24 wherein the amount of deoxyuridine is at least 1 μmol and no greater than 3 μmol, based on 1 ml of total blood culture.

26. The process of claim 11 wherein the deoxyuridine suppression test is effected by incubation with deoxyuridine in an amount of 2 μmol, based on 1 ml of total blood culture.

27. The process of claim 13 wherein the amount of thymidine is at least 1 μmol and no greater than 3 mol, based on 1 ml of total blood culture.

28. The process of claim 1 wherein the mitogen to whole blood sample ratio is no greater than 40 μg per 0.1 ml of whole blood sample.

29. The process of claim 13 wherein the mitogen to whole blood sample ratio is no greater than 40 μg per 0.1 ml of whole blood sample.

30. The process of claim 20 wherein the mitogen to whole blood sample ratio is no greater than 40 μg per 0.1 ml. of whole blood sample.

* * * * *